(12) United States Patent
Weekes et al.

(10) Patent No.: US 6,692,469 B1
(45) Date of Patent: Feb. 17, 2004

(54) INJECTION DEVICES

(75) Inventors: Stuart Weekes, Oxford (GB); Steven Mark Guy Rolfe, Oxon (GB)

(73) Assignee: Ares-Trading S.A., Vaumarcus (CH)

( * ) Notice: Subject to any disclaimer, the term of this patent is extended or adjusted under 35 U.S.C. 154(b) by 0 days.

(21) Appl. No.: 09/463,748

(22) PCT Filed: Jul. 30, 1998

(86) PCT No.: PCT/GB98/02287
§ 371 (c)(1),
(2), (4) Date: Jan. 31, 2000

(87) PCT Pub. No.: WO99/06100
PCT Pub. Date: Feb. 11, 1999

(30) Foreign Application Priority Data

Jul. 31, 1997 (GB) .............................. 9716065

(51) Int. Cl.⁷ ................................ A61M 5/32
(52) U.S. Cl. ...................... 604/197; 604/137; 604/157; 604/187
(58) Field of Search ................ 604/181, 187, 604/196, 218, 220, 228, 232, 240, 257, 186, 117, 134, 135, 136, 137, 110, 198, 197, 195, 156, 131, 157

(56) References Cited

U.S. PATENT DOCUMENTS

| | | | |
|---|---|---|---|
| 3,292,776 A | | 12/1966 | Penn |
| 4,880,410 A | * | 11/1989 | Rossmark .................. 604/110 |
| 5,092,376 A | * | 3/1992 | Blankenship et al. ......... 141/25 |
| 5,137,516 A | * | 8/1992 | Rand et al. ................ 604/136 |
| 5,167,641 A | * | 12/1992 | Schmitz ..................... 604/196 |
| 5,451,210 A | * | 9/1995 | Kramer et al. .............. 604/137 |
| 5,709,662 A | * | 1/1998 | Olive et al. ................ 604/135 |
| 5,893,845 A | * | 4/1999 | Newby et al. .............. 604/198 |
| 5,951,516 A | * | 9/1999 | Bunyan ...................... 604/143 |
| 6,391,003 B1 | * | 5/2002 | Lesch, Jr. ................... 604/110 |

FOREIGN PATENT DOCUMENTS

| | | |
|---|---|---|
| EP | 0 666 084 | 8/1995 |
| FR | 2 623 403 | 5/1989 |
| FR | 2 654 938 | 5/1991 |
| WO | WO 88/06463 | 9/1988 |
| WO | WO 95/31235 | 11/1995 |

* cited by examiner

*Primary Examiner*—Glenn K. Dawson
*Assistant Examiner*—Jennifer Maynard
(74) *Attorney, Agent, or Firm*—Young & Thompson

(57) ABSTRACT

An injection device has a barrel (1) for housing and guiding a syringe (13) as it is urged forward to project its needle (14), while the dose is ejected, and as a return spring (22) retracts it. A firing mechanism (6) is connectable to the rear end of the barrel and is re-usable, whereas the barrel (1) with its spent syringe (13) is disposable. The connection (4) has limited freedom of axial movement so that, once made, forward pressure on the firing mechanism (6) moves the syringe (13) up to a ready position. A number of barrels (1) with syringes (13) can be housed in a common box (31) with a single firing mechanism (6), the forward end of each barrel (1) being screwed to a locator (32) on the base of the box. The engagement of the firing mechanism (16) with the rear end of each barrel (1) is also screw-threaded, but of opposite hand, so that screwing the firing mechanism (6) on and continuing to turn releases the complete device; and correspondingly the barrel (1) can be returned and located in the box (31) while the firing mechanism (6) is separated from it.

9 Claims, 3 Drawing Sheets

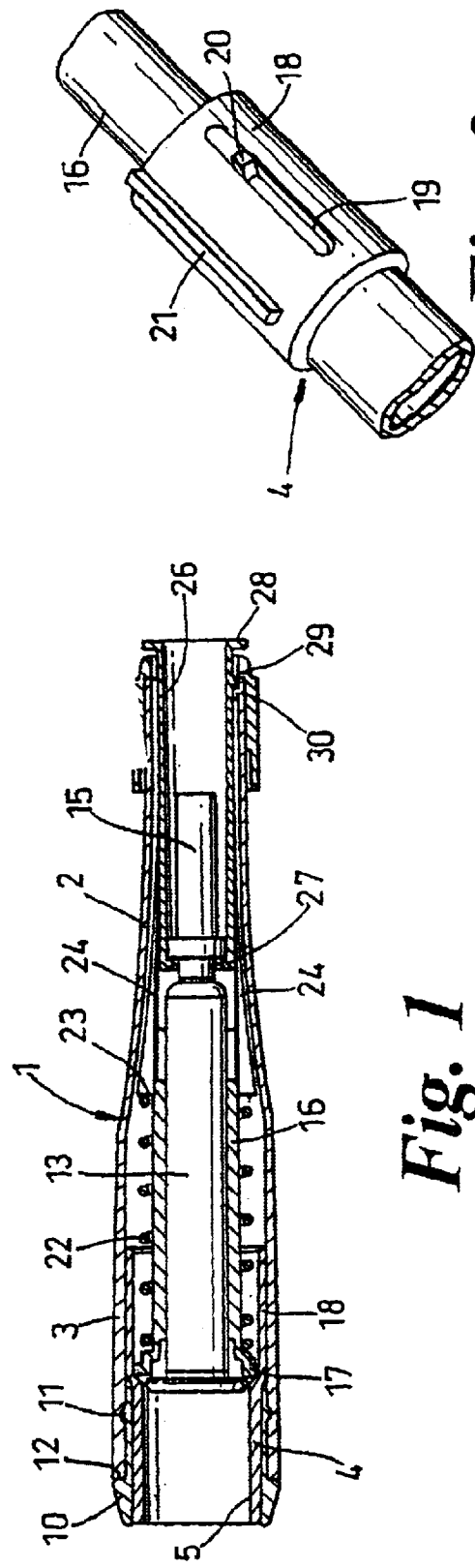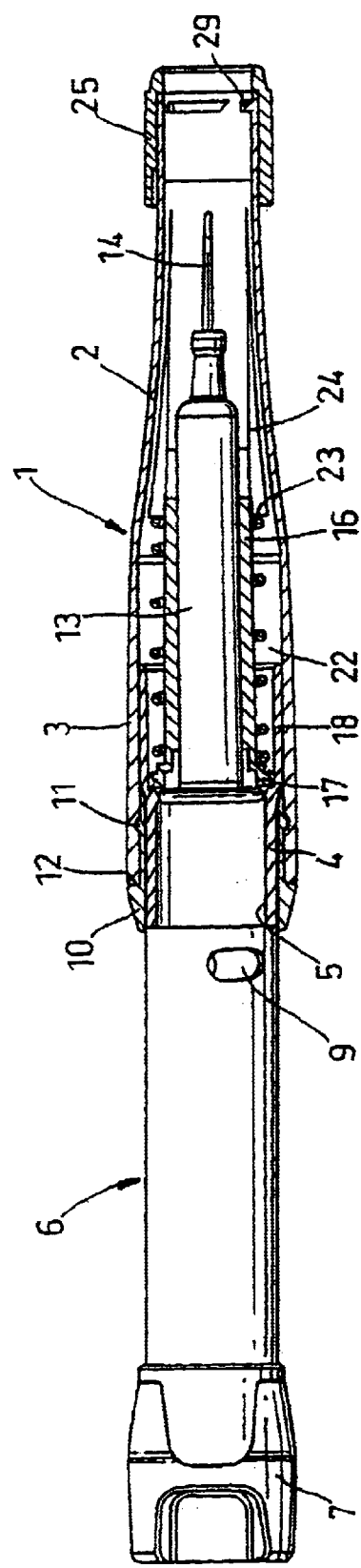

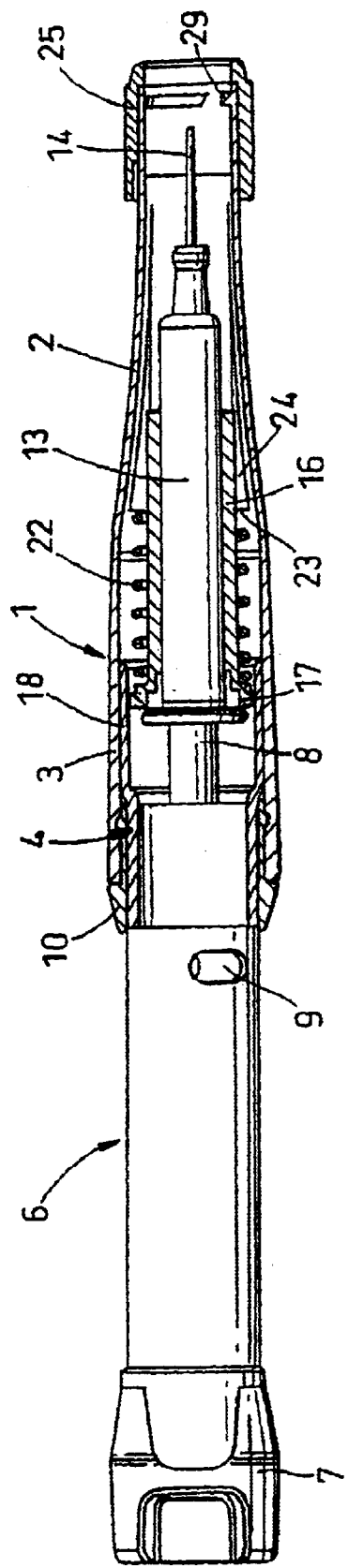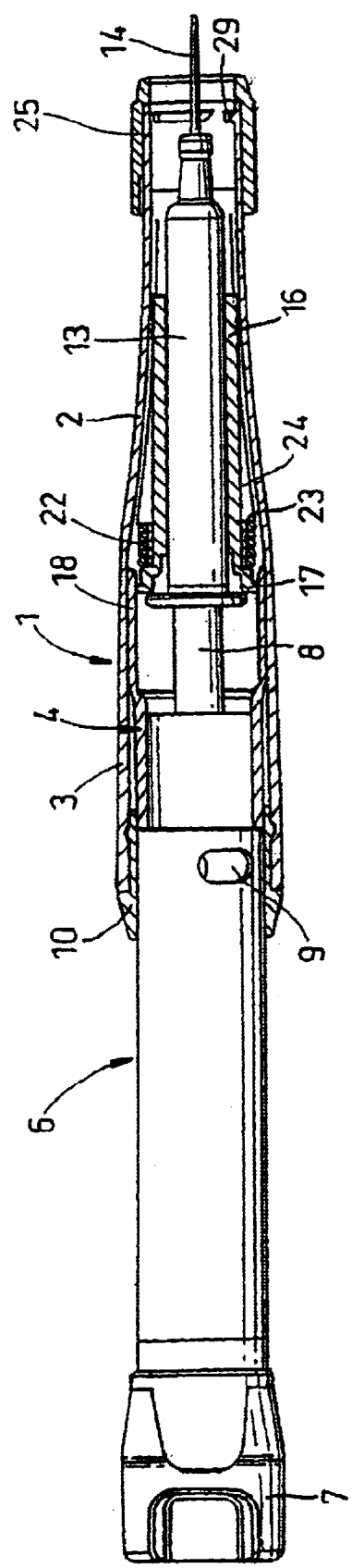
Fig. 5
Fig. 4

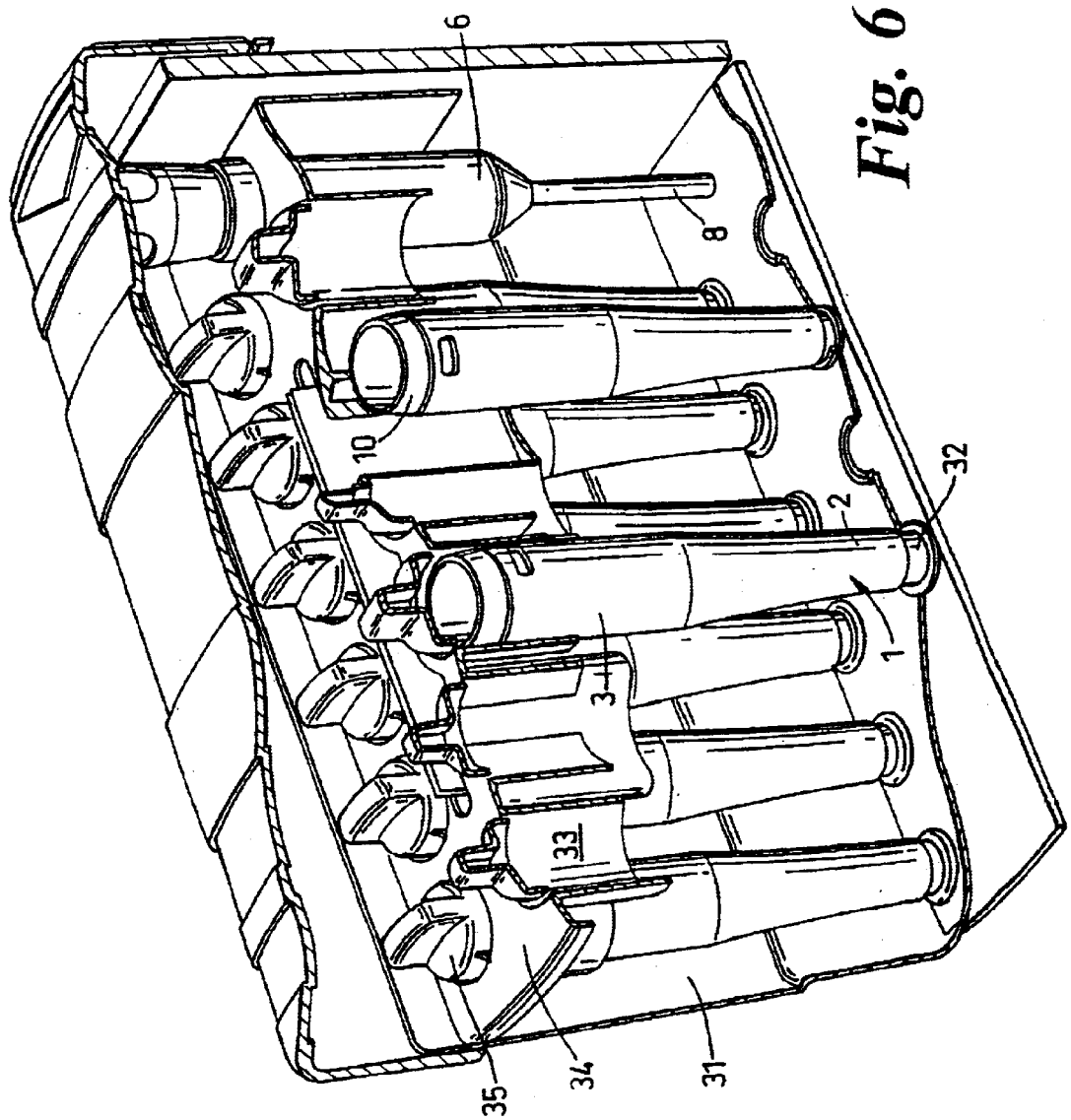

INJECTION DEVICES

FIELD OF THE INVENTION

This invention relates to injection devices.

BACKGROUND OF THE INVENTION

After any injection, the syringe with its needle is thrown away into a guarded enclosure, for obvious safety reasons. But removing it from a re-usable device that first fires the syringe forwards to make the needle penetrate, then pushes the syringe piston forwards to eject the dose, and which finally withdraws the syringe and needle, can itself be hazardous and time-consuming.

One answer is to discard everything, but such injection devices are complex and expensive. That is not therefore a realistic option.

However, by making the device in two parts, one being a re-usable firing mechanism with a plunger that can be released to spring forwards, and the other being a housing and guide for the syringe to which the firing mechanism can be temporarily attached, it becomes possible to contemplate throwing away this other part (still containing a syringe).

It is the aim of this invention to provide such a device.

SUMMARY OF THE INVENTION

According to one aspect of the present invention there is provided an injection device comprising a barrel, a syringe carrier within the barrel axially movable between a rearward position, in which the needle of a syringe carried thereby is retracted within the forward end of the barrel, and a forward position, in which the needle projects from the forward end of the barrel, spring means urging the carrier towards the rearward position, and a firing mechanism with a firing member which, when released, acts on the piston in the syringe to urge the syringe forwards and then to eject a dose, characterised in that the firing mechanism is separable from the barrel and in that there is a connector with limited freedom of axial movement at the rear end of the barrel for attachment of the firing mechanism, the connector initially being held at a rearward position by the spring means acting through the syringe carrier, but moving to a forward position, taking the syringe carrier with it, as the barrel is held against the skin by the firing device being pressed forwards, the syringe carrier then being in an intermediate position from which it can be propelled to its forward position on actuation of the firing mechanism, and the connector reverting under the influence of the spring means to its rearward position after removal of the injection device from the skin.

The spring means will act through the carrier, the syringe, the firing member and its device to cause the reversion of the connector to its rearward position.

Conveniently, the attachment is by mating screw threads, the connector being restrained against rotation with respect to the barrel.

The connector may be a stepped tube, the smaller diameter portion at the rear end providing a socket to receive the firing device, the internal forward facing shoulder formed by the step providing an abutment for the rear end of the syringe carrier, and the external, rearward facing shoulder formed by the step providing an abutment for engagement with a locking ring, fitted to the rear end of the barrel, when the connector is at its rearward position.

The syringe carrier may have a lost-motion connection with the connector, and this will define the limit of the carrier's forward movement. The larger diameter portion of the stepped tube connector may have axially parallel slots in which projections from the rear end of the syringe carrier engage to form the lost-motion connection.

The barrel will generally be internally equipped with guide means for keeping the syringe carrier co-axial therewith.

The spring means is conveniently a coil spring surrounding the syringe carrier to engage a flange at the rear end thereof and reacting against an abutment within the barrel. This abutment may be provided by the rear end of the guide means.

Preferably, the forward end of the barrel is equipped with means for effectively altering its length and thus the amount by which the needle of the syringe will project.

According to another aspect of the present invention there is provided injection equipment comprising a plurality of disposable syringe devices which have retracted needles in the pre-use and post-use conditions, a firing mechanism which can be screw-fitted to the rear end of each device, and a housing for said devices, the leading ends of each syringe device being screw-threadedly engageable with locators in the housing, these screw threads being of opposite hand to that of the firing mechanism whereby, for use of a syringe device located in the housing, the firing mechanism is screwed to its rear end and the screw action continued until the syringe device releases from its locator, and post-use the syringe device is screwed back on its locator using the firing mechanism and the screw action continued until the firing mechanism releases from the syringe device.

Preferably each pre-use syringe device has a rear end cap removable to allow screw attachment of the firing mechanism.

BRIEF DESCRIPTION OF THE DRAWINGS

For a better understanding of the invention one embodiment will now be described, by way of example, with reference to the accompanying drawings, in which:

FIG. 1 is an axial section of an injection device as supplied, without any firing mechanism.

FIG. 2 is an axial section of the device with the firing mechanism fitted, and ready for use, FIG. 3 is a detail, in perspective, of part of the injection device, FIG. 4 is an axial section of the device, with its firing mechanism, during injection, FIG. 5 is an axial section of the device, with its firing mechanism, after use, and FIG. 6 is a cutaway perspective view of a housing for is a set of injection devices.

DETAILED DESCRIPTION OF THE INVENTION

An injection device has a barrel 1 with a tapered forward part 2 and a generally cylindrical rearward part 3. Telescoped into this rearward part 3 and prevented from rotating by a splined engagement (not fully shown) there is stepped connector tube 4 whose lesser diameter rear end provides a socket 5 into which a firing mechanism 6 is screwed. This is of a known kind having a trigger button 7 at its rear end which, when pressed, causes a plunger 8 to project from its forward end. It also has a window 9 through which can be seen marks indicating whether it has been fired or not. The tube 4 is made captive to the barrel 1 by a snap-in locking ring 10 which sleeves between the part 3 and the socket 5 and engages the barrel 1 by a circumferential rib and groove arrangement 11 and a shoulder 12. The ring 10 is therefore effectively integral with the barrel 1, and its forward end provides an annular shoulder against which the external step in the tube 4 normally abuts, preventing escape of that tube.

Within the barrel 1 there is a syringe comprising a capsule 13 with a needle 14 at its forward end, initially shielded by a needle cap 15. The capsule is enclosed over most of its length by a sleeve 16, which has an outwardly projecting flange 17 at its rear end initially abutting the internal step of the tube 4. This forms a syringe carrier. As seen in FIG. 3, this carrier has a lost-motion connection within the connector 4, whose large diameter forward end 18 has longitudinal slots 19 in which lugs 20 projecting from the flange 17 engage. An anti-rotation spline 21 can also be seen in FIG. 3. A coil spring 22 surrounds the sleeve 16, its rear end, within the connector 4, engaging the flange 17 and its forward end abutting internal shoulders 23 provided by the rear ends of fin-like guides 24 within the tapered portion 2 which keep the syringe aligned during injection. Initially this spring 22 is unstressed.

Fitted around the forward end of the part 2 there is a nose piece. 25, which is smoothly rounded comfortably to abut the user's skin and which can be adjusted to lengthen and shorten the barrel and thereby alter the depth of needle penetration.

In the initial state, a tubular insert 26 projects into the tapered part 2 beyond the needle cap 15, where it has an inturned rim 27 engaging behind the enlarged base of the cap 15. Outside the forward end of the barrel 1 the insert can be grasped by a flange 28. Within the mouth of the forward part 2 of the barrel there are studs 29 which co-operate with screw-threading 30 on the exterior of the insert 26. This is of coarse pitch and of opposite hand to the screw-threading in the socket 5.

For use, the firing mechanism 6 is screwed into the socket 5 and the complete injection assembly is parted from the insert 26 which pulls the cap 15 off the needle .14. Because of the opposite hand threads, screwing away the insert 26 does not undo the fixing mechanism 6 for the socket 5.

The injector is then applied to the skin of the user, and the firing device 6 urged forward. This carries the tube 4 forwards, telescoping further into the rear part 3 of the barrel 1, which of course is held static by its engagement with the patient. This movement continues until the connector 4 is arrested, conveniently by the anti-rotation spline(s) 21 meeting the end(s)of the associated groove(s) in the barrel. During this movement, the spring 22 is partially compressed and the syringe is also carried forwards, but the needle 14 is not quite projected beyond the nose piece 25.

The button 7 is then pressed and the plunger 8 shoots forward engaging the piston (not shown) in the capsule, first projecting the capsule, with its carrier 16, forwards and causing the needle to pierce the skin. The carrier is stopped by the lugs 20 meeting the forward ends of the slots 19, but the plunger 8 carries on to eject the dose (FIG. 4).

Finally, the injector is withdrawn, and the spring 22 exerts itself. During the injection, it has been fully compressed, but now it re-expands, urging the capsule carrier 16 rearwardly, and taking with it the capsule, thereby withdrawing the needle safely within the barrel. At the same time, through the plunger 8, the whole firing mechanism 6 is shifted rearwardly with the connector 4, until the outer step in the connector 4 engages the ring 10 (FIG. 5).

The firing mechanism 6 is then separated from the injection device, and the latter can be thrown away while the firing mechanism is reusable.

The insert 26 may be a separate item as shown in FIG. 1, or it could be one of several fixed to and upstanding from the bottom of a case 31 as shown in FIG. 6, each insert (now referenced 32) being fitted with an injection device as shown in previous Figures. The barrels 1 are upright and their cylindrical portions 3 locate in tubular guides 33 depending from an apertured, horizontal partition 34. The locking rings 10 are just below the partition and so the devices are not readily accessible. A single firing mechanism 6 which can be fitted to each injection device in turn is also supplied within the case and located by the partition 34.

When such a device is to be used, a cap 35 covering the socket 5 and proud of the partition 34 is removed and thrown away, and the firing mechanism 6 is taken out, entered through the aperture in the partition, and screwed into the socket. When it reaches its fully mated position, the user carries on turning in the same direction and this rotates the barrel 1. The studs 29 are forced up the screw-threading 30 to lift the injection device until it is free to be drawn clear of the case 31.

After use, the injection device is replaced, being turned by the firing mechanism 6 to screw down onto the insert 32. When it is fully on, continued turning screws the firing mechanism 6 free of the socket 5. The empty socket (not re-covered by the throwaway cap) indicates that the syringe of that injection device is spent.

What is claimed is:

1. An injection device formed as two separate assemblies, the first assembly comprising a barrel having forward and rear ends, a syringe carrier for a syringe with a needle within the barrel axially movable between a rearward position, in which the needle of the syringe carried thereby is retracted within the forward end of the barrel, and a forward position, in which the needle projects from the forward end of the barrel, spring means urging the carrier towards the rearward position, and a connector, and the second assembly comprising a firing mechanism with a firing member which, when released, acts on the syringe to urge the syringe forwards to said forward position and then to eject a dose, wherein the firing mechanism is separable from the barrel and in that the connector has limited freedom of axial movement at the rear end of the barrel and is configured for attachment of the firing mechanism, the connector initially being held at a rearward position by the spring means acting through the syringe carrier, but moving to a forward position, taking the syringe carrier with it, as the barrel is held against the skin by the firing mechanism being pressed forwards, the syringe carrier then being in a position intermediate said forward and rearward positions of said syringe carrier from which said syringe carrier can be propelled to said forward position of said syringe carrier on actuation of the firing mechanism, and the connector reverting under the influence of the spring means to said rearward position after removal of the injection device from the skin.

2. An injection device as claimed in claim 1, characterised in that the attachment is by mating screw threads, the connector being restrained against rotation with respect to the barrel.

3. An injection device as claimed in claim 1, characterised in that the connector is a stepped tube creating a smaller diameter portion, at a rear end thereof and a larger diameter portion at a forward end thereof, the smaller diameter portion at the rear end providing a socket to receive the firing member the stepping in the tube defining an internal forward facing shoulder providing an abutment for a rear end of the syringe carrier, and the stepping in the tube also defining an external, rearward facing shoulder providing an abutment for engagement with a locking ring, fitted to the rear end of the barrel, when the connector is at its rearward position.

4. An injection device as claimed in claim 3, characterised in that the syringe carrier has a lost-motion connection with the connector, this defining the limit of the carrier's forward movement.

5. An injection device as claimed in claim 4, characterised in that the larger diameter portion of the stepped tube connector has axially parallel slots in which projections from the rear end of the syringe carrier engage to form the lost-motion connection.

6. An injection device as claimed in claim 1, characterised in that the barrel is internally equipped with guide means, having forward and rear ends, for keeping the syringe carrier co-axial therewith.

7. An injection device as claimed in claim 6, characterised in that the spring means is a coil spring having forward and rear ends and surrounding the syringe carrier to engage a flange at said rear end and reacting against an abutment within the barrel.

8. An injection device as claimed in claim 7, characterised in that the abutment is provided by the rear end of the guide means.

9. An injection device as claimed in claim 1, characterised in that the forward end of the barrel is equipped with means for effectively altering the barrel length and thus the amount by which the needle of the syringe will project.

* * * * *